(12) United States Patent
Midorikawa et al.

(10) Patent No.: US 7,514,589 B2
(45) Date of Patent: Apr. 7, 2009

(54) METHOD FOR PRODUCING AROMATIC IODIDES

(75) Inventors: Koji Midorikawa, Chiba (JP); Hiroshi Takahoso, Mobara (JP); Junichi Yoshida, Kyoto (JP); Seiji Suga, Kyoto (JP)

(73) Assignees: Nippoh Chemicals Co., Ltd., Chuo-Ku, Tokyo (JP); Kyoto University, Kyoto-Shi, Kyoto (JP)

( * ) Notice: Subject to any disclaimer, the term of this patent is extended or adjusted under 35 U.S.C. 154(b) by 16 days.

(21) Appl. No.: 11/794,817

(22) PCT Filed: Dec. 28, 2005

(86) PCT No.: PCT/JP2005/024130

§ 371 (c)(1),
(2), (4) Date: Sep. 24, 2007

(87) PCT Pub. No.: WO2006/073124

PCT Pub. Date: Jul. 13, 2006

(65) Prior Publication Data

US 2008/0146853 A1 Jun. 19, 2008

(30) Foreign Application Priority Data

Jan. 6, 2005 (JP) .............................. 2005-001693

(51) Int. Cl.
*C07C 17/152* (2006.01)
(52) U.S. Cl. .................................................... 570/206
(58) Field of Classification Search .................. 570/206
See application file for complete search history.

(56) References Cited

U.S. PATENT DOCUMENTS

| | | | |
|---|---|---|---|
| 4,666,570 | A | 5/1987 | Matsuoka et al. |
| 5,734,073 | A | 3/1998 | Chambers et al. |
| 5,856,596 | A | 1/1999 | Nukada |
| 6,437,203 | B1 | 8/2002 | Shintou et al. |
| 6,802,640 | B2 | 10/2004 | Schubert et al. |
| 6,851,846 | B2 | 2/2005 | Fujii et al. |
| 2002/0005762 | A1 | 1/2002 | Roth |
| 2003/0215479 | A1 | 11/2003 | Sendelbach et al. |
| 2004/0011413 | A1 | 1/2004 | Fujii et al. |

FOREIGN PATENT DOCUMENTS

| | | |
|---|---|---|
| EP | 0 376 858 (A2) | 7/1990 |
| EP | 1 595 862 A1 | 11/2005 |
| JP | 62-063527 A | 3/1987 |
| JP | 5-313386 A | 11/1993 |
| JP | 7-233106 A | 9/1995 |
| JP | 9-503527 A | 4/1997 |
| JP | 2000-319209 A | 11/2000 |
| JP | 2003-001077 A | 1/2003 |
| JP | 2003-502144 A | 1/2003 |
| JP | 2003-321325 A | 11/2003 |
| JP | 2004-016904 A | 1/2004 |
| JP | 2004-099443 A | 4/2004 |
| JP | 2004-262769 A | 9/2004 |

OTHER PUBLICATIONS

Form PCT/ISA/210 (International Search Report) dated Feb. 28, 2006).
Form PCT/ISA/237 (Written Opinion of the International Searching Authority) dated Feb. 28, 2006.
English language version of Form PCT/ISA/237 (Written Opinion of the International Searching Authority) dated Feb. 14, 2005.
M.-A. Schneider et al., "A Microreactor-Based System for the Study of Fast Exothermic Reactions in Liquid Phase: Characterization of the System", Chemical Engineering Journal, 2004, vol. 101, pp. 241-250, Elsevier (cited in the International Search Reported dated Feb. 26, 2006, previously filed on Jul. 6, 2007 in the above-identified application).
Herman O. Wirth et al., "Jodierung Aromatischer Verbindungen Mit Jod Und Jodsäure, I", Ann., 1960, vol. 634, pp. 84-103 (with partial English translation), cited on p. 2 of the specification.
J. Chem. Soc., Jap., 1971, vol. 92, pp. 1021-1023 (with English comments), cited on p. 2 of the specification.
P. Rumpf, "Memoires Presentes a la Societe Chimique", Bull. So. Chem., 1940, vol. 7, pp. 634-638 (with partial English translation), cited on p. 2 of the specification.
Larry L. Miller et al., Iodination With Electrolytically Generated Iodine(I):Journal of the American Chemical Society, May 6, 1970, vol. 92, No. 9, pp. 2821-2825.
Larry L. Miller et al., "Scope and Mechanism of Aromatic Iodination With Electrochemically Generated Iodine(I)", Journal of the American Chemical Society, Mar. 17, 1976, vol. 98, No. 6, pp. 1515, 1519.
Wolfgang Ehrfeld, et al., "Characterization of Mixing in Micromixers by a Test Reaction: Single Mixing Units and Mixer Arrays", Ind. Eng. Chem. Res., 1999, vol. 38, No. 3, pp. 1075-1082, American Chemical Society.

*Primary Examiner*—Sikarl A Witherspoon
(74) *Attorney, Agent, or Firm*—Buchanan Ingersoll & Rooney PC

(57) ABSTRACT

The present invention is directed to provide a means, which enables production of a product superior in color tone in high yield by using an easy-to-handle and highly safe technique, in a method for producing an aromatic iodide. The present invention relates to a method for producing an aromatic iodide, characterized in that an aromatic compound and an active iodinating agent are fed into a flow reactor equipped with a high-speed mixer and hydrogen atom on the aromatic ring of said aromatic compound is continuously substituted by iodine atom.

20 Claims, 2 Drawing Sheets

METHOD FOR PRODUCING AROMATIC IODIDES

TECHNICAL FIELD

The present invention relates to a method for producing aromatic iodides, in more detail, the present invention relates to a method for producing aromatic iodides using a flow reactor equipped with a high-speed mixer.

BACKGROUND ART

Aromatic iodides are important compounds as intermediates for various electronic materials and medicinal drugs, due to high reactivity thereof. For example, developments of organic photoreceptors for electrophotography, which have a structure of laminated charge-generating layers and charge-transporting layers, have been actively promoted, and as a charge-transporting material to be used for such charge-transporting layer, various types of triarylamine compounds have been proposed (see, JP-A-5-313386), where aromatic iodides are used as an intermediate in the synthesis of such triarylamine compounds. The triarylamine compound can be synthesized by a coupling reaction of an arylamine compound with an aryl halide using a copper catalyst, and aryl iodine compounds are often used as an aryl halide. This is because use of bromide as a halogenating agent results in significantly low reactivity in the coupling reaction (conversion to tertiary amine) at final stage.

Besides the above-described use, aromatic iodides are widely used, therefore, various methods for synthesizing iodinated material of aromatic compounds have been proposed. For example, a method for iodinating an aromatic compound using iodic acid and iodine in a mixed solvent of water and acetic acid, in the presence of sulfuric acid catalyst (see, Ann. 634, 84 (1960)), a method for iodinating an aromatic compound using periodic acid and iodine in a mixed solvent of water and acetic acid, in the presence of sulfuric acid catalyst (see, J. Chem. Soc. Jap. 92, 1021 (1971)), or a method of synthesis via Sandmeyer reaction from corresponding amino compound as shown by the following scheme (see, Bull. Soc. Chem., 7, 634 (1940)):

≤ Sandmeyer reaction (Halobenzen Synthesis) ≥

[Chemical Formula 1]

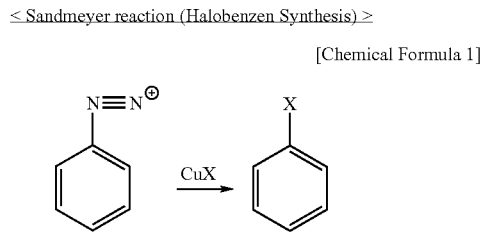

On the other hand, when reactivity of the iodinating agent is high, or when an aromatic compound, which tends to undergo easily electrophilic substitution reaction by a functional group, is iodized, a mixture of mono-iodized product and di-iodized product is obtained, and it is sometimes difficult to obtain mono-iodized product selectively. To solve this problem, for example, a method to improve selectivity for mono-iodination by reducing molar ratio of iodine to react with an aromatic compound has been proposed (see, JP-A-7-233106). Specifically, the publication describes that when an aromatic compound is iodized using iodic acid, periodic acid or iodine as a iodinating agent in a mixed solvent of water and acetic acid, a high purity of mono-iodized product can be obtained by setting a ratio of the number of iodine atom to the number of an aromatic compound molecule to be reacted to a level less than 1, more preferably less than 0.5.

At the same time, various types of reactors are used in the production steps of these compounds. For example, emulsion concoctions have been produced using a flow reactor having a micro-structure unit such as micro-mixer with a micro-channel of, generally, several to several hundreds μm (generally, generically referred to as "micro-reactor") (see, JP-A-2003-321325). Since emulsion concoctions influence on the quality and the like of the final product depending on the degree of homogenization, a good homogenization is obtained by using a micro-mixer, in view of the conventional technology where a sufficient effect can not be exerted due to uneven emulsified particles.

Furthermore, in carrying out Friedel-Crafts type alkylation reaction to an aromatic compound, a method for synthesizing mono-alkylated product efficiently by using a micro-mixer to improve mixing efficiency has been disclosed (see, JP-A-2004-99443). According to the application, when two kinds of liquids to be mixed are fed into a reaction vessel having a volume of several ml or more to be mixed, since assemblies of relatively large fluid clusters spreads to the whole reaction vessel coarsely, followed by diffusing by turbulent flow of vortex while becoming finer gradually and then being mixed, if mixing time is sufficiently longer than reaction time, local unevenness in concentration greatly influences on the reaction; on the contrary, since mixing occurs by molecular diffusion in a micro-channel, very rapid mixing is attained, and by using a micro-mixer, a high selectivity can be obtained.

In addition, the micro-reactor has features such as (1) heating/cooling speeds are fast, (2) flow is laminar flow, (3) surface area per unit volume is large, (4) reaction proceeds rapidly due to shorter diffusion length of material.

DISCLOSURE OF INVENTION

Here, according to the technology described in Bull. Soc. Chem. 7, 634 (1940), when an aromatic compound is iodized by using Sandmeyer reaction, formation of di-iodized product is suppressed. However, there are such problems that since an amino compound to be used as a raw material is highly toxic, the method described in the above literature has a problem in handling and safety of the raw material, and that treatment after the reaction is complicated as well as yield is low. In addition, according to the technology described in JP-A-7-233106, by reducing a ratio of the number of iodine atom to be reacted to the number of an aromatic compound molecule to 0.5, formation of di-iodized product can be suppressed and mono-iodized product can be obtained selectively. However, by the above method, a large amount of raw material remains in the reaction system after the reaction, and a purification step is additionally required to remove the raw material, as well as productivity is also low.

In addition, the reaction in which an aromatic compound is iodized by using iodic acid or periodic acid can proceed very smoothly. However, for example, in the mono-iodination reaction using the conventional technique, the product becomes a mixture of mono-iodized product and di-iodized product. There is such a problem that if amino compound is synthesized by carrying out amination reaction using such a mixture as it is, the product resulting from the amination naturally becomes a mixture, resulting in lowered electric characteristics of charge-transporting material. Furthermore, in the iodination reaction using the conventional technique, there is such a phenomenon specific to the iodination reaction that the product takes on iodine color and thereby a purification step is additionally required. Halides of aromatic compounds have large molecular weights which make purification by distillation and the like difficult. Thus, there is such a problem that a technique of very high cost has to be employed for purification of aromatic iodides, resulting in raised production cost.

Furthermore, according to the technology described in the above JP-A-2004-99443, in the Friedel-Crafts type alkylation reaction, mono-alkylated product can be synthesized efficiently by using a micro-mixer, however, there has not been reported that the micro-mixing is effective in the iodinating reaction of aromatic compounds.

Thus, it is an object of the present invention to provide a means, which enables production of a product having superior color tone (colorless or less-colored) in high yield by using an easy-to-handle and highly safe technique, in a method for producing an aromatic iodide.

The inventors of the present invention have intensively studied a way to solve the above problems. As the results, the inventors have found that in the reaction using an aromatic compound and an active iodinating agent in which a hydrogen atom on an aromatic ring in the above aromatic compound is substituted by an iodine atom, continuous synthesis using a flow reactor equipped with a high-speed mixer is effective. Further, the inventors have found that according to this technique (micro-flow system), an iodized product introduced with desired moles of iodine atom can be selectively obtained without reducing the ratio of the number of iodine atom to the number of molecule of the aromatic compound to be reacted. Thus, the present invention was accomplished based on the above knowledge.

Namely, the present invention relates to a method for producing an aromatic iodide, characterized in that an aromatic compound and an active iodinating agent are fed into a flow reactor equipped with a high-speed mixer and hydrogen atom on the aromatic ring of the above aromatic compound is continuously substituted by iodine atom.

Further objects, features and characteristics of the present invention will become clear from the preferred embodiments exemplified with descriptions and attached drawings below.

BEST MODE FOR CARRYING OUR THE INVENTION

Figure 1:
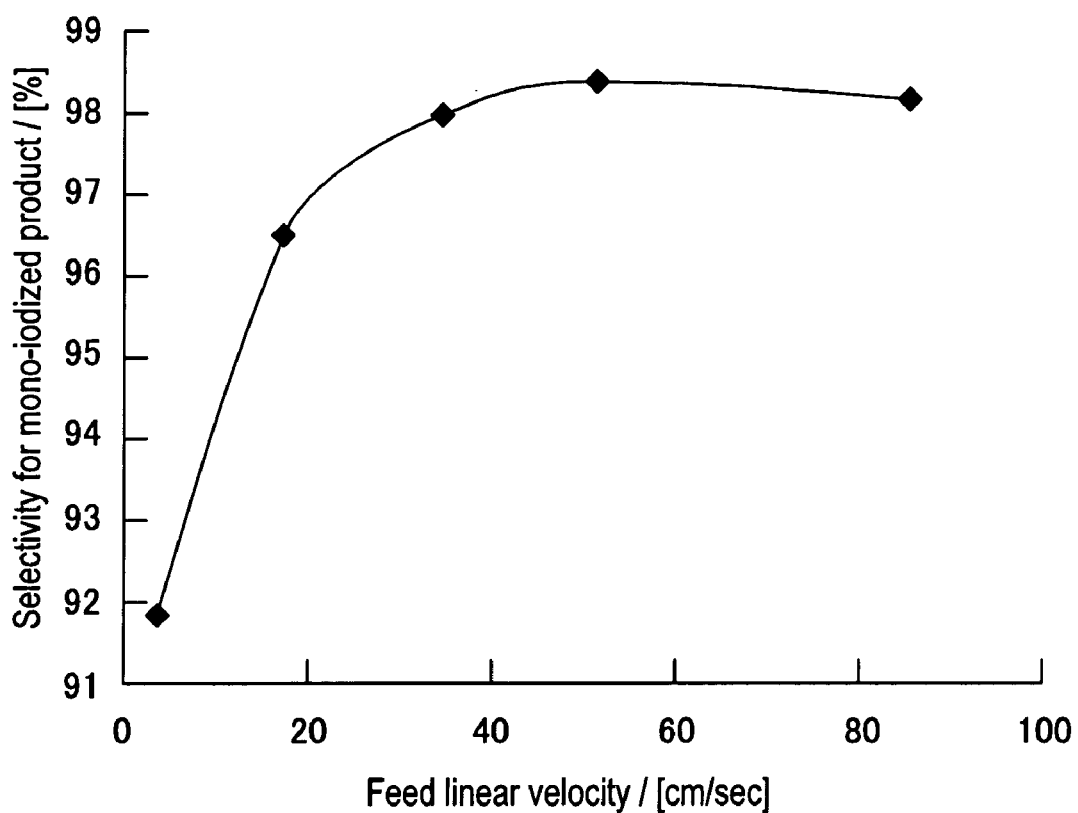
FIG. 1 is a graph showing a relationship between selectivity for mono-iodized product and feed linear velocity in Examples 1-1 to 1-5.

Hereinafter, the mode for carrying out the present invention will be explained in detail.

The present invention relates to a method for producing an aromatic iodide, characterized in that an aromatic compound and an active iodinating agent are fed into a flow reactor equipped with a high-speed mixer (hereinafter, referred to as "micro-reactor") and hydrogen atom on the aromatic ring of the above aromatic compound is continuously substituted by iodine atom.

According to the present invention, an aromatic iodide having superior color tone can be prepared in high yield using an easy-to-handle and highly safe technique, by continuously iodinating an aromatic compound using a flow reactor equipped with a high-speed mixer. It should be noted that, the mechanism by which an aromatic iodide having superior color tone can be produced by the production method of the present invention has not been completely clarified, but it is presumed that selectivity for a desired aromatic iodide (for example, mono-iodized product) can be improved because hydrogen atom on the aromatic ring of the aromatic compound is substituted by a desired mole number of iodine. In this regard, the above mechanism is absolutely based on presumption, and even if the effect of the present invention is practically obtained by a mechanism other than the above mechanism, the technical scope of the present invention is not limited by the above mechanism in any way.

Hereinafter, the production method of the present invention will be explained in detail in the order of the steps.

Firstly, an aromatic compound and an active iodinating agent of raw materials are provided.

The "aromatic compound" which is one of raw materials in the production method of the present invention is an aromatic compound having 2 or more hydrogen atoms bonding to the aromatic ring. This comes from the following reason. Namely, when an aromatic compound having only one hydrogen atom bonding to the aromatic ring is used as a raw material, since there is only one hydrogen atom to be substituted by iodine, that is, only mono-iodized product can be obtained, the object of the present invention, that is, obtaining a product having superior color tone can be attained without using the present invention.

In addition, as an aromatic compound to be used in the production method of the present invention, any of those that have been conventionally used as a raw material of aromatic iodides can be widely included within the intended compounds, so long as the compound can be fed into a micro-reactor described later. Further, optionally, even a compound that has not been conventionally used for iodination reaction may be used as an aromatic compound of the present invention. As such a compound, for example, aromatic compounds having 6 to 30 carbon atoms are suitably used, and examples thereof include monocyclic aromatic hydrocarbon compound such as benzene; condensed polycyclic aromatic hydrocarbon compound such as pentalene, indene, naphthalene, azulene, heptalene, biphenylene, fluorene, phenalene, phenanthrene, anthracene, fluoranthene, acephenanthrylene, triphenylene, pyrene, naphthacene, and the like; and heterocyclic aromatic compound such as pyridine, pyridazine, indole, quinoline, isoquinoline, quinazoline, purine, carbazol, benzoxazol, thianthrene, and the like. These aromatic compounds may be substituted by, for example, alkyl group having 1 to 20 carbon atoms, hydroxyl group, amino group, alkoxy group having 1 to 20 carbon atoms, aryloxy group, phenyl group which may have a substituent such as halogen (Cl, Br, I), and the like.

In the present invention, preferably an aromatic compound, which may form di-iodized product or tri-iodized product and the like as a by-product when 1 mole of an active iodinating agent is reacted to 1 mole of an aromatic compound, is used because the effect of the present invention can be more clearly exhibited. Examples of such aromatic compound include, specifically, anisole, tert-butylbenzene, 1,2-dimethoxybenzene, 1,3-dimethoxybenzene, 1,4-dimethoxybenzene, o-xylene, m-xylene, p-xylene, toluene, fluorene, biphenyl, naphthalene, 9,10-dihydrophenanthrene, anthracene, p-hydroxybenzoic acid, m-terphenyl, p-terphenyl, 1,3,5-triphenylbenzene, triphenylamine, phenyl ether, fluorobenzene, phenyl acetate, aminoethylbenzene, phenol, mesitylene, 1,3,5-trimethoxybenzene, 1,2,4-trimethoxybenzene, and the like. Among them, anisole, tert-butylbenzene, 1,2-dimethoxybenzene, 1,3-dimethoxybenzene, 1,4-dimethoxybenzene, fluorene, biphenyl, 1,10-dihydrophenanthrene, m-terphenyl and p-terphenyl are preferably used.

"Active iodinating agent" which is another raw material in the production method of the present invention is not particularly limited, and includes, for example, iodine, iodine monochloride, iodic acid, periodic acid, hydroiodic acid, potassium iodide, sodium iodide, N-iodosuccinimide, N,N'-diiodo-5,5-dimethylhydantoin, bis-pyridineiodonium tetrafluoroborate, and the like. In addition, a compound that comprises iodonium cation as a reaction activator to be generated by electrolytic oxidation of iodine or electrolytic oxidation of iodine compound and a compound that comprises iodonium cation as a reaction activator to be generated by oxidation of iodine or iodine compound with an oxidizing agent can also be used as an active iodinating agent in the present invention. Here, an oxidizing agent to generate the reaction activator includes, but is not limited to, for example, persulfuric acid, iodic acid, periodic acid, and the like. Among them, a compound that generates iodonium cation as a reaction activator by oxidation of iodine or iodine compound with an oxidizing agent, iodine monochloride, N-iodosuccinimide, N,N'-diiodo-5,5-dimethylhydantoin, bis-pyridineiodonium tetrafluoroborate, and the like are preferably used. These compounds are suitable because use of these compounds as an active iodinating agent allows presence of activated iodonium cation in the solution in the case of a solution, enabling feeding into a micro-reactor in the form of solution and direct reaction with a solution of aromatic compound. It should be noted that, the above-described "a compound that generates iodonium cation as a reaction activator by electrolytic oxidation of iodine or electrolytic oxidation of iodine compound" can be prepared by the conventional known method. For example, the above-described compound can be obtained in the anode chamber by using an electrolytic cell having platinum electrodes and isolated by glass filter, with the anode being charged with a mixed solution of tetrabutylammonium tetrafluoroborate in acetonitrile and iodine and the cathode being charged with tetrabutylammonium tetrafluoroborate in acetonitrile and trifluoromethanesulfonic acid, applying current at around 2 to 2.2 F/mol of electric quantity to iodine while cooling.

In a preferable mode of the present invention, the active iodinating agent is introduced into the flow reactor in a ratio of (m−0.4) moles to (m+0.4) moles (based on iodine atom) (m means an integer satisfying: $1 \leq m \leq n-1$) to 1 mole of the aromatic compound having not less than n (n means an integer of 2 or more) hydrogen atoms bonding to the aromatic ring. Thereby, the hydrogen atom is substituted by m moles of iodine. Stoichiometrically, in order to prepare a m-moles-iodized product, m moles of active iodinating agent may be used to 1 mole of an aromatic compound. However, by introducing the above range of active iodinating agent without being limited to the above stoichiomety, an aromatic iodide in which the hydrogen atom(s) bonding to the aromatic ring of the aromatic compound has (have) been substituted by m iodine atom(s) can be prepared selectively. It should be noted that, when an amount of the active iodinating agent to be fed is less than (m−0.4) moles, a ratio of the iodized product which is substituted by (m−1) moles of iodine increases (that is, selectivity for the m-moles-iodized product is lowered), requiring in some case separation and purification, resulting in raised production cost. On the contrary, when an amount of the active iodinating agent to be fed is over (m+0.4) moles, a ratio of the iodized product which is substituted by (m+1) moles of iodine increases in reverse (that is, selectivity for the m-moles-iodized product is similarly lowered), requiring also in some case separation and purification, resulting in raised production cost.

The flow reactor equipped with a high-speed mixer to be used in the present invention is a reaction apparatus of a type in which a fluid continuously flows in, reacts, and flows out of the system, and specific form thereof is not particularly limited so long as the apparatus has at least 2 fluid mixing sections and a tubular reaction section communicating with the mixing sections. Therefore, any of agitated vessel type reactor, tubular type reactor, and the like can be suitably used. The flow reactor may be commercially available one or homemade one.

Generally, since reaction control becomes difficult when reaction rate is faster than diffusing rate, reaction solution is mixed by means of agitation and the like so that diffusion rate becomes faster than reaction rate. The high-speed mixer equipped to the flow reactor is used as the means for this mixing, and specific form thereof is not particularly limited so long as reaction solution is mixed so that diffusion rate becomes faster than reaction rate. However, when reaction rate is faster than the diffusion rate which is increased by means of conventional mechanical agitation, mixing, or the like, use of a flow reactor (micro-reactor) equipped with an apparatus (micro-mixer) capable of increasing diffusion rate by utilizing micro-space as a high-speed mixer, to make diffusion rate faster than reaction rate, has a beneficial effect on the reaction control, and particularly suitable. In the reaction system where reaction rate is faster than diffusion rate, when reaction is carried out in a macro space, side reaction easily progresses because main reaction is completed before reaction solution becomes homogeneous allowing reagent being locally present excessively. However, when the micro-mixer is used, occurrence of side reaction is suppressed because mixing is carried out rapidly and homogeneously. In other word, in another preferable embodiment of the present invention, in a high-speed mixer equipped to a flow reactor, mixing time of an aromatic compound and an active iodinating agent is shorter than reaction time of an aromatic compound and an active iodinating agent. By such embodiment, further improvement of selectivity can be attempted because an aromatic compound and an active iodinating agent can be mixed before side reaction progresses.

Specific form of the micro-reactor to be used in the present invention is not particularly limited, but equivalent diameter of a channel for each liquid is preferably 1 to 10,000 µm, more preferably 10 to 500 µm, and particularly preferably 20 to 100 µm. Equivalent diameter below 1 µm is disadvantageous because pressure for feeding becomes high, and equivalent diameter over 10,000 µm sometimes results in inferior homogenization after mixing. Further, mixing system in the high-speed mixer is also not particularly limited, and any of slit type or distribution and recombination type may be employed. It should be noted that, "equivalent diameter" means a diameter of a circle calculated from a cross-section of channel when the cross-section of channel is assumed to be circular. In the present invention, however, the cross-section of channel is not limited only to circular form.

In the present invention, sum of feed linear velocity of each solution in feeding an aromatic compound and an active iodinating agent into a micro-reactor is 10 cm/second or more, preferably 15 cm/second or more, and particularly preferably 50 cm/second or more. The sum of the feed linear velocities under 10 cm/second is disadvantageous because sufficient mixing cannot be obtained and selectivity is lowered.

Other specific forms of the micro-reactor are not particularly limited, and conventionally known knowledge (for example, JP-A-2003-502144, JP-A-2003-1077, and the like) may be referred to as appropriate.

In the production method of the present invention, by using the micro-reactor as a reactor, raw materials come into contact immediately and mixing and reaction of raw materials with each other are facilitated. Accordingly, reaction can proceed rapidly and reaction time can be shortened. For example, when m moles of an active iodinating agent is fed to 1 mole of an aromatic compound, since both chemicals are mixed in a ratio of 1:m in a micro space and reaction proceeds, generation of by-product is suppressed, and as a result, mono-iodized product can be effectively produced.

In a preferable mode of the present invention, in particular, when it is intended to prepare mono-iodized product in high selectivity, an active iodinating agent is fed into a micro-reactor in a ratio of 0.6 to 1.4 mole (based on iodine atom), preferably 0.9 to 1.3 mole, and particularly preferably 0.9 to 1.0 mole to 1 mole of an aromatic compound. As shown in Examples described below, when iodine obtained by electrolytic oxidation as an active iodinating agent and 1,3-dimethoxybenzene as an aromatic compound were used, and both chemicals were reacted in a ratio of 1:1 in acetonitrile solvent to prepare mono-iodized product of 1,3-dimethoxybenzene, selectivity for mono-iodized product was 98.6% and selectivity for di-iodized product was 1.4%. Thus, according to the present invention, without reducing ratio of the number of iodine atom to the number of aromatic compound molecule to be reacted, mono-iodized product can be obtained in high selectivity as well as in high yield. Here, the reaction scheme is shown below.

each of the batch system and the micro-flow system of the present invention are shown in Table 1 below.

TABLE 1

[Chemical Formula 3]

| | Para:Ortho (mono-iodized product) | Mono-iodized product: Di-iodized product |
|---|---|---|
| Batch system | 85:15 | 95:5 |
| Micro-flow system | 81:19 | 98:2 |

In the present invention, when an aromatic compound is reacted with an active iodinating agent, which can be prepared more selectively than those by the conventional technology (batch system), main structural formulae for mono-iodized product and main structural formulae for di-iodized product are shown below.

[Chemical Formula 2]

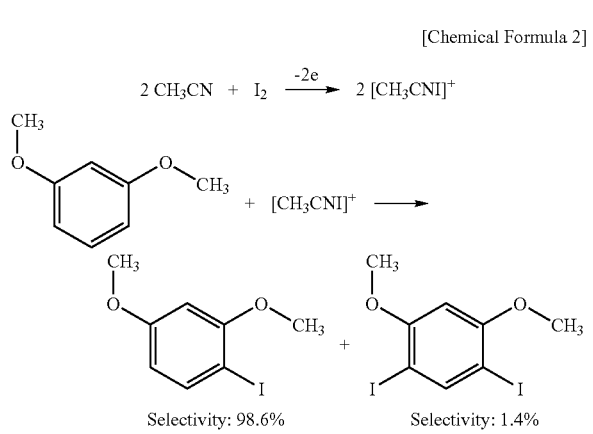

Selectivity: 98.6%  Selectivity: 1.4%

In addition, when it is intended to obtain mono-iodized product according to the above-described preferable embodiment, formation of by-products such as di-iodized product and tri-iodized product is suppressed and selectivity for mono-iodized product can be improved, but substitution site of iodine is not controlled. Therefore, when substitution by iodine occurs, mono-iodized product can be prepared in high yield while orientation of substitution conforms to the conventional chemical principle. In the case of 1,3-dimethoxybenzen shown in the above-described example, 2-position and 5-position are difficult to be substituted by iodine from the orientation characteristics thereof. Reaction of anisole and an active iodinating agent is shown below, mono-iodized product is obtained as a mixture of ortho-substituted product and para-substituted product. Here, production rates of ortho-substituted product and para-substituted product with regard to mono-iodized product and ratio of the production rates for mono-iodized product and di-iodized product (selectivity) for

[Chemical Formula 4]

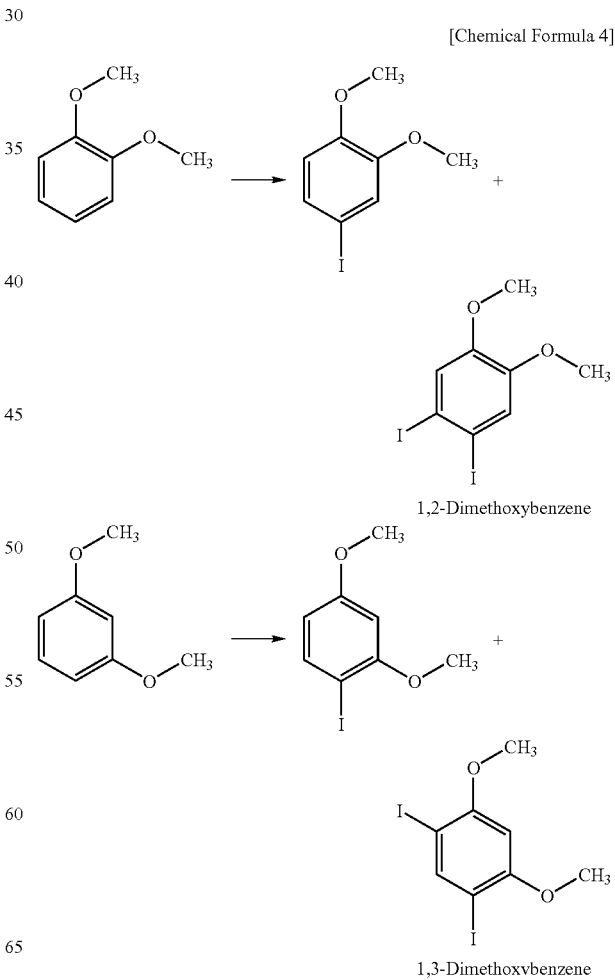

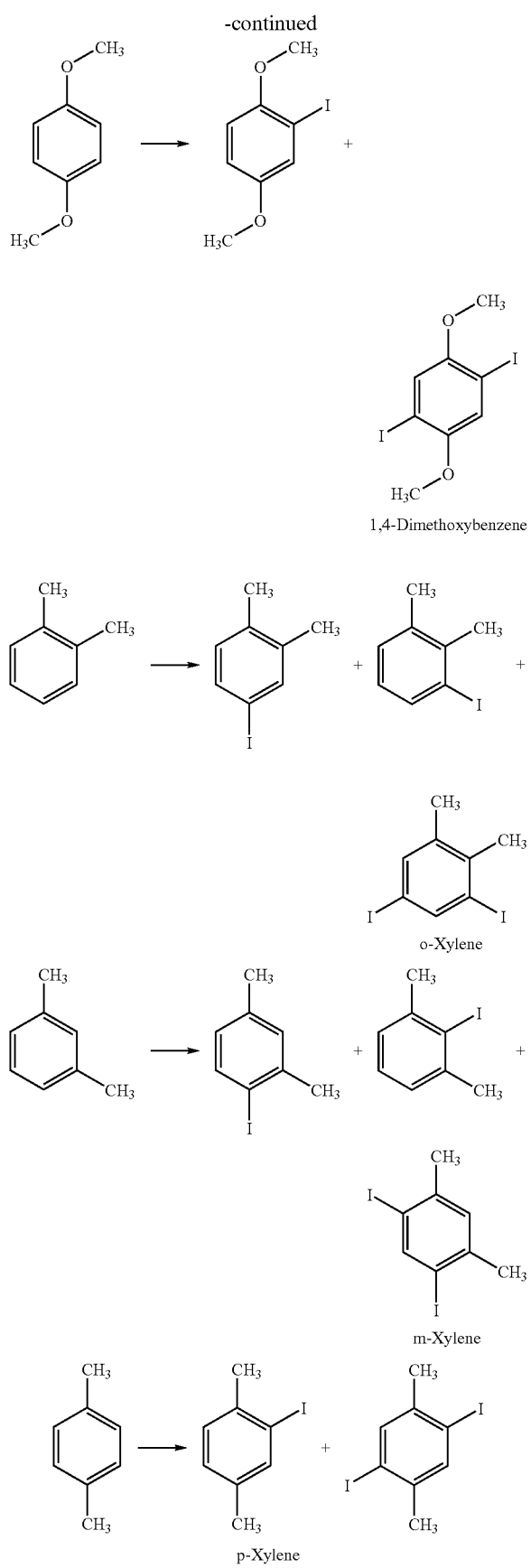
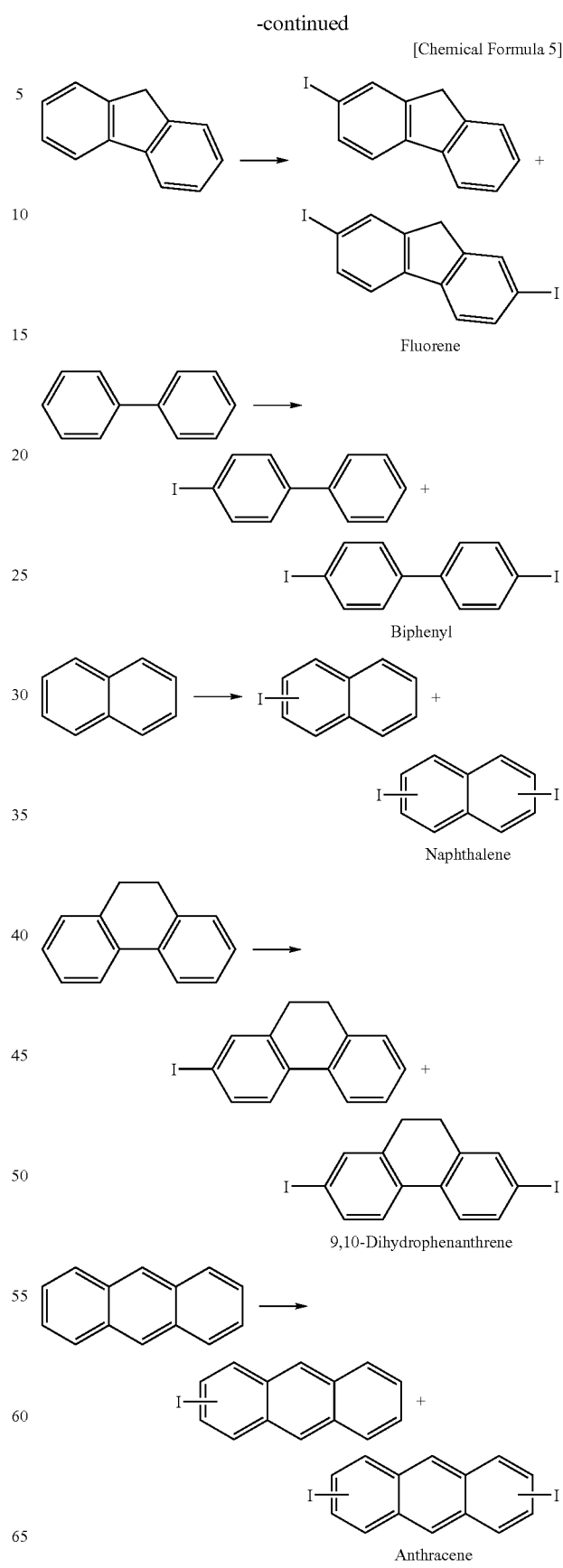

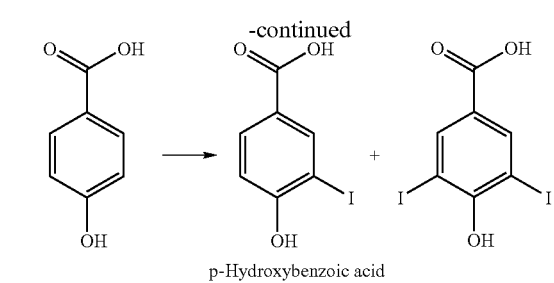
p-Hydroxybenzoic acid

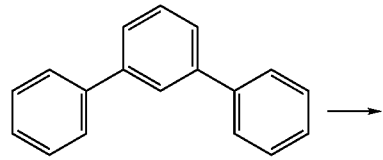

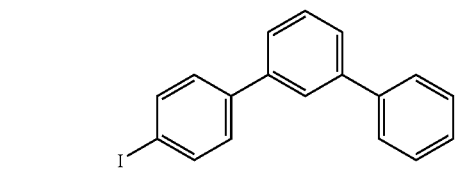
m-terphenyl

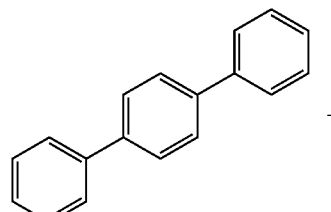

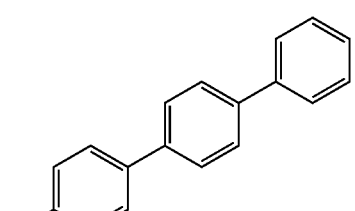

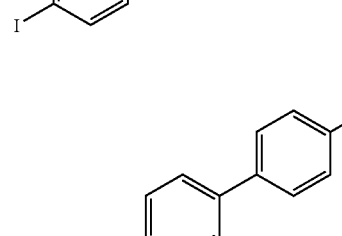
p-terphenyl

In a preferable embodiment of the present invention, in particular, when it is intended to prepare di-iodized product in high selectivity, an active iodinating agent is fed into a micro-reactor in a ratio of 1.6 to 2.4 mole (based on iodine atom), preferably 1.8 to 2.3 mole, and particularly preferably 2.0 to 2.2 mole to 1 mole of an aromatic compound. According to such embodiment, not only di-iodized product can be synthesized in high selectivity, but also reaction progresses efficiently and yield of di-iodized product can be also improved, due to efficient diffusion mixing in a micro-reactor.

Furthermore, in particular, when it is intended to prepare tri-iodized product in high selectivity, an active iodinating agent is fed into a micro-reactor in a ratio of 2.6 to 3.4 mole (based on iodine atom), preferably 2.8 to 3.3 mole, and particularly preferably 2.9 to 3.2 mole to 1 mole of an aromatic compound. For example, when mono-iodized product, di-iodized product and tri-iodized product are each useful as an intermediate to other product or the like, these products can be prepared and isolated by feeding an aromatic compound and an active iodinating agent into a micro-reactor in the above-described molar ratio. Structures of main mono-iodized product, di-iodized product and tri-iodized product of 1,3,5-triphenylbenzene and triphenylamine are shown below.

[Chemical Formula 6]

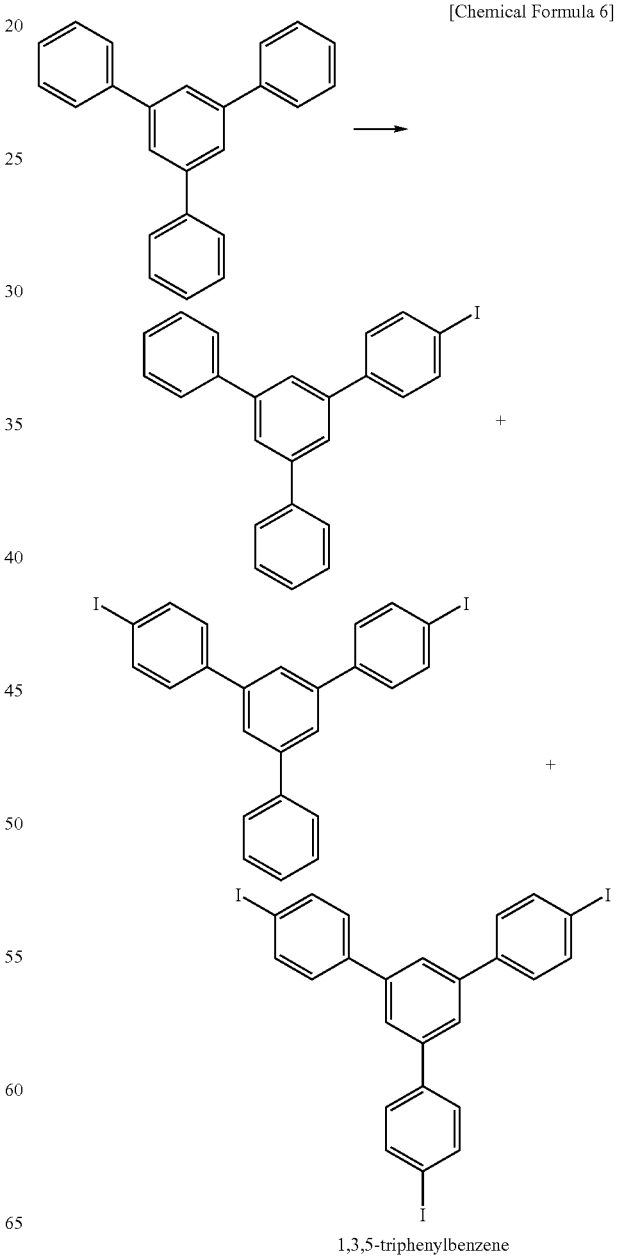
1,3,5-triphenylbenzene

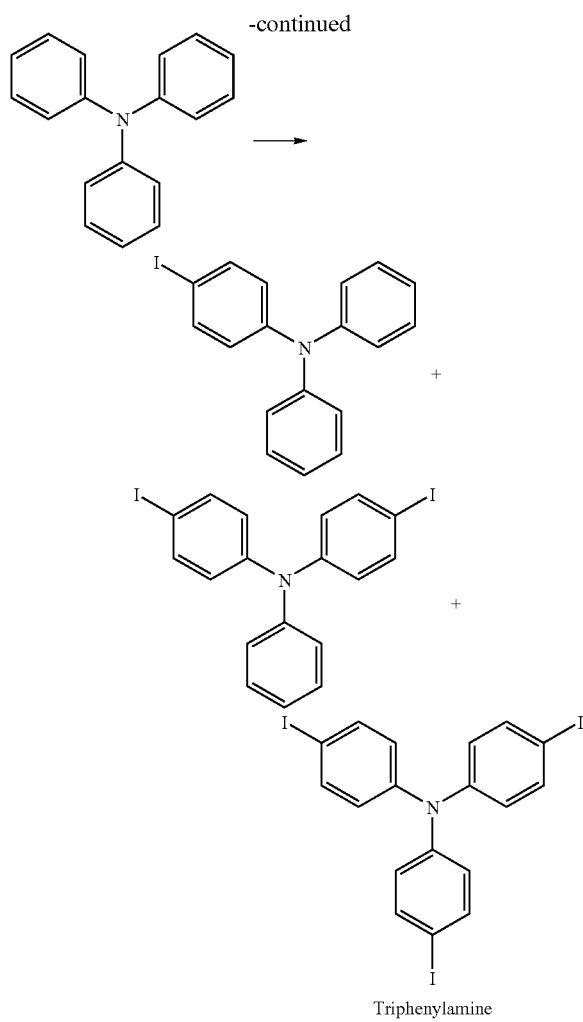

Triphenylamine

In the present invention, an aromatic compound and an active iodinating agent are generally fed into a micro-reactor each in a form of solution dissolving these compounds in a solvent, or in a form of dispersion dispersing them in a solvent.

Solvent to dissolve an aromatic compound is preferably one, which is easily separable after reaction and dissolve both of the aromatic compound and the aromatic iodide obtained without reacting with an active iodinating agent. Such solvent includes acetonitrile, dichloromethane, chloroform, carbon tetrachloride, propanol, iso-propanol, butanol, dimethylformamide, dimethylacetoamide, and the like.

At the same time, solvent to dissolve an active iodinating agent includes acetonitrile, dichloromethane, chloroform, carbon tetrachloride, methanol, ethanol, propanol, iso-propanol, butanol, iso-butanol, dimethylformamide, dimethylacetoamide, and the like.

The present invention is characterized in that an aromatic compound and an active iodinating agent are fed into a micro-reactor to promote reaction, and reaction temperature may be selected as appropriate corresponding to the compound to be used and the reaction system. In addition, reaction time, that is, residence time in the reaction section of the micro-reactor may be also selected as appropriate corresponding to the reaction system.

The aromatic iodide prepared according to the production method of the present invention is useful for technology fields such as manufacturing of organic EL materials, manufacturing of medicines, and the like. In particular, according to the present invention, since occurrence of the colored product problem, which had been a specific problem in the iodinating reaction, can be effectively suppressed, rising of the production cost resulting from additional purification step is avoided, aromatic iodides can be prepared at a low cost by using an easy-to-handle and safe technique.

EXAMPLES

Next, the present invention will be specifically explained referring to Examples, however, these Examples should not be construed to limit the present invention in any way.

Reference Example

Into an anode solution chamber of a H-type double electrolytic cell equipped with platinum electrodes and a stirring bar and isolated with a glass filter, 8 ml of a solution of 127 mg (0.5 mmol) of iodine and 0.3 M tetrabutylammonium tetrafluoroborate in acetonitrile were charged. Into a cathode solution chamber thereof, 8 ml of a solution of 79 mg (0.526 mmol) of trifluoromethanesulfonic acid and 0.3 M tetrabutylammonium tetrafluoroborate in acetonitrile were charged. The cell was then cooled down to 0 to 5° C. on an ice-water bath, and a current of 10 mA was applied at an electric quantity of 2 F/mol, while the solution was stirred with a magnetic stirrer. As a result, electrolytically oxidized iodine corresponding to 1.0 mmol could be obtained in the anode solution chamber. This solution in the anode solution chamber was used as an active iodinating agent in Examples described below.

Example 1-1

A flow reactor, in which a Teflon tube having an outer diameter of 1/16 inch, an inner diameter of 0.5 mm, and a length of 2 m, as a reaction section, was connected to an exit of a high-speed mixer (produced by IMM, Trade Name: SIMM-V2) having an equivalent diameter of 80 μm, was provided. To the feed inlet of the high-speed mixer, a syringe was connected via a Teflon tube having an outer diameter of 1/16 inch and an inner diameter of 0.5 mm.

Into a 100 ml Erlenmeyer flask, 30 ml of a saturated sodium bicarbonate aqueous solution, 1 ml of a saturated sodium thiosulfate aqueous solution, and 30 ml of diethyl ether were charged, and the solution was cooled to 0° C. on an ice-water bath while stirred with a magnetic stirrer. The high-speed mixer and the reaction section were also immersed into an ice-water bath to be cooled to 0° C. The exit of the reaction section was introduced into water layer in the Erlenmeyer flask.

Total amount of the active iodinating agent obtained in the above-described Reference Example was connected to the feed tube of the high-speed mixer. 138 mg (1.0 mmol) of 1,3-dimethoxybenzene was dissolved in the same amount of acetonitrile as that of the active iodinating agent, and then the resultant solution was charged into the 10 ml syringe, which was connected to the feed tube of the high-speed mixer.

Each syringe was set on a syringe pump, and flow rate from each syringe was adjusted to be 3.0 ml/min. The iodinating reaction was initiated by feeding each solution into the high-speed mixer. Sum of feed linear velocity for each solution was 50.9 cm/sec. The reaction solution obtained by the reaction displayed pale yellow color.

After completion of feeding solutions, the aqueous layer and the ether layer were separated. The ether layer was concentrated in vacuo, and the residue was loaded on a 10 cm silica gel column, followed by elution of reaction products from the column with 100 ml of ether. The solvent was concentrated in vacuo, and then 30 ml of a saturated sodium bicarbonate aqueous solution and 50 ml of hexane were added thereto, to carry out extraction. Two layers were separated, and the hexane layer was concentrated to dryness in vacuo, to yield 223.9 mg of a reaction product.

NMR analysis and GC analysis of the reaction product gave 19.6 mg of 1,3-dimethoxybenzene, 199.7 mg (0.756 mmol) of 4-iodo-1,3-dimethoxybenzene and 4.7 mg (0.012 mmol) of 4,6-diiodo-1,3-dimethoxybenzene. Namely, ratio of the production rates of mono-iodized product and di-iodized product was 98.4:1.6.

Example 1-2

Iodinating reaction and post-treatment were carried out under the similar conditions to those in Example 1-1, except that the feed flow rate was changed to 0.2 ml/min, to obtain 256.7 mg of a reaction product. In this case, the sum of feed linear velocity for each solution was 3.4 cm/sec. The reaction solution obtained by the reaction displayed pale yellow color.

NMR analysis and GC analysis of the reaction product gave 24.5 mg of 1,3-dimethoxybenzene, 205.2 mg (0.777 mmol) of 4-iodo-1,3-dimethoxybenzene and 26.9 mg (0.069 mmol) of 4,6-diiodo-1,3-dimethoxybenzene. Namely, ratio of the production rates of mono-iodized product and di-iodized product was 91.8:8.2.

Example 1-3

Iodinating reaction and post-treatment were carried out under the similar conditions to those in Example 1-1, except that the feed flow rate was changed to 1.0 ml/min, to obtain 219.3 mg of a reaction product. In this case, the sum of feed linear velocity for each solution was 17.0 cm/sec. The reaction solution obtained by the reaction displayed pale yellow color.

NMR analysis and GC analysis of the reaction product gave 16.0 mg of 1,3-dimethoxybenzene, 193.1 mg (0.731 mmol) of 4-iodo-1,3-dimethoxybenzene and 10.2 mg (0.026 mmol) of 4,6-diiodo-1,3-dimethoxybenzene. Namely, ratio of the production rates of mono-iodized product and di-iodized product was 96.6:3.4.

Example 1-4

Iodinating reaction and post-treatment were carried out under the similar conditions to those in Example 1-1, except that the feed flow rate was changed to 2.0 ml/min, to obtain 209.3 mg of a reaction product. In this case, the sum of feed linear velocity for each solution was 34.0 cm/sec. The reaction solution obtained by the reaction displayed pale yellow color.

NMR analysis and GC analysis of the reaction product gave 18.4 mg of 1,3-dimethoxybenzene, 185.3 mg (0.702 mmol) of 4-iodo-1,3-dimethoxybenzene and 5.5 mg (0.014 mmol) of 4,6-diiodo-1,3-dimethoxybenzene. Namely, ratio of the production rates of mono-iodized product and di-iodized product was 98.0:2.0.

Example 1-5

Iodinating reaction and post-treatment were carried out under the similar conditions to those in Example 1-1, except that the feed flow rate was changed to 5.0 ml/min, to obtain 221.3 mg of a reaction product. In this case, the sum of feed linear velocity for each solution was 84.9 cm/sec. The reaction solution obtained by the reaction displayed pale yellow color.

NMR analysis and GC analysis of the reaction product gave 19.5 mg of 1,3-dimethoxybenzene, 193.4 mg (0.732 mmol) of 4-iodo-1,3-dimethoxybenzene and 3.5 mg (0.009 mmol) of 4,6-diiodo-1,3-dimethoxybenzene. Namely, ratio of the production rates of mono-iodized product and di-iodized product was 98.8:1.2.

Example 1-6

A flow reactor, in which a Teflon tube having an outer diameter of 1/16 inch, an inner diameter of 0.5 mm, and a length of 2 m, as a reaction section, was connected to an exit of a high-speed mixer (produced by IMM, Trade Name: SIMM-V2) having an equivalent diameter of 80 μm, was provided. To the feed inlet of the high-speed mixer, a syringe was connected via a Teflon tube having an outer diameter of 1/16 inch and an inner diameter of 0.5 mm.

Into a 100 ml Erlenmeyer flask, 30 ml of a saturated sodium bicarbonate aqueous solution, 1 ml of a saturated sodium thiosulfate aqueous solution, and 30 ml of diethyl ether were charged, and the solution was cooled to 0° C. on an ice-water bath while stirred with a magnetic stirrer. The high-speed mixer and the reaction section were also immersed into an ice-water bath to be cooled to 0° C. The exit of the reaction section was introduced into water layer in the Erlenmeyer flask.

Total amount of the active iodinating agent obtained in the above-described Reference Example was connected to the feed tube of the high-speed mixer. 138 mg (1.0 mmol) of 1,2-dimethoxybenzene was dissolved in the same amount of acetonitrile as that of the active iodinating agent, and then the resultant solution was charged into the 10 ml syringe, which was connected to the feed tube of the high-speed mixer. Each syringe was set on a syringe pump, and flow rate from each syringe was adjusted to be 3.0 ml/min. The iodinating reaction was initiated by feeding each solution into the high-speed mixer. Sum of feed linear velocity for each solution was 50.9 cm/sec. The reaction solution obtained by the reaction displayed pale yellow color.

After completion of feeding solutions, the aqueous layer and the ether layer were separated. The ether layer was concentrated in vacuo, and the residue was loaded on a 10 cm silica gel column, followed by elution of reaction products from the column with 100 ml of ether. The solvent was concentrated in vacuo, and then 30 ml of a saturated sodium bicarbonate aqueous solution and 50 ml of hexane were added thereto, to carry out extraction. Two layers were separated, and the hexane layer was concentrated to dryness in vacuo, to yield 178.8 mg of a reaction product.

NMR analysis and GC analysis of the reaction product gave 15.3 mg of 1,2-dimethoxybenzene, 161.8 mg (0.613 mmol) of 4-iodo-1,2-dimethoxybenzene and 2.9 mg (0.007 mmol) of 4,5-diiodo-1,2-dimethoxybenzene. Namely, ratio of the production rates of mono-iodized product and di-iodized product was 98.9:1.1.

Example 1-7

A flow reactor, in which a Teflon tube having an outer diameter of 1/16 inch, an inner diameter of 0.5 mm, and a length of 2 m, as a reaction section, was connected to an exit of a high-speed mixer (produced by IMM, Trade Name:

SIMM-V2) having an equivalent diameter of 80 μm, was provided. To the feed inlet of the high-speed mixer, a syringe was connected via a Teflon tube having an outer diameter of 1/16 inch and an inner diameter of 0.5 mm.

Into a 100 ml Erlenmeyer flask, 30 ml of a saturated sodium bicarbonate aqueous solution, 1 ml of a saturated sodium thiosulfate aqueous solution, and 30 ml of diethyl ether were charged, and the solution was cooled to 0° C. on an ice-water bath while stirred with a magnetic stirrer. The high-speed mixer and the reaction section were also immersed into an ice-water bath to be cooled to 0° C. The exit of the reaction section was introduced into water layer in the Erlenmeyer flask.

Total amount of the active iodinating agent obtained in the above-described Reference Example was connected to the feed tube of the high-speed mixer. 138 mg (1.0 mmol) of 1,4-dimethoxybenzene was dissolved in the same amount of acetonitrile as that of the active iodinating agent, and then the resultant solution was charged into the 10 ml syringe, which was connected to the feed tube of the high-speed mixer. Each syringe was set on a syringe pump, and flow rate from each syringe was adjusted to be 3.0 ml/min. The iodinating reaction was initiated by feeding each solution into the high-speed mixer. Sum of feed linear velocity for each solution was 50.9 cm/sec. The reaction solution obtained by the reaction displayed pale yellow color.

After completion of feeding solutions, the aqueous layer and the ether layer were separated. The ether layer was concentrated in vacuo, and the residue was loaded on a 10 cm silica gel column, followed by elution of reaction products from the column with 100 ml of ether. The solvent was concentrated in vacuo, and then 30 ml of a saturated sodium bicarbonate aqueous solution and 50 ml of hexane were added thereto, to carry out extraction. Two layers were separated, and the hexane layer was concentrated to dryness in vacuo, to yield 222.3 mg of a reaction product.

NMR analysis and GC analysis of the reaction product gave 19.9 mg of 1,4-dimethoxybenzene, 185.2 mg (0.701 mmol) of 3-iodo-1,4-dimethoxybenzene and 17.2 mg (0.044 mmol) of 3,6-diiodo-1,4-dimethoxybenzene. Namely, ratio of the production rates of mono-iodized product and di-iodized product was 94.1:5.9.

Example 1-8

A flow reactor, in which a Teflon tube having an outer diameter of 1/16 inch, an inner diameter of 0.5 mm, and a length of 2 m, as a reaction section, was connected to an exit of a high-speed mixer (produced by IMM, Trade Name: SIMM-V2) having an equivalent diameter of 80 μm, was provided. To the feed inlet of the high-speed mixer, a syringe was connected via a Teflon tube having an outer diameter of 1/16 inch and an inner diameter of 0.5 mm.

Into a 100 ml Erlenmeyer flask, 30 ml of a saturated sodium bicarbonate aqueous solution, 1 ml of a saturated sodium thiosulfate aqueous solution, and 30 ml of diethyl ether were charged, and the solution was cooled to 0° C. on an ice-water bath while stirred with a magnetic stirrer. The high-speed mixer and the reaction section were also immersed into an ice-water bath to be cooled to 0° C. The exit of the reaction section was introduced into water layer in the Erlenmeyer flask.

Total amount of the active iodinating agent obtained in the above-described Reference Example was connected to the feed tube of the high-speed mixer. 166.7 mg (1.00 mmol) of fluorene was dissolved in the same amount of acetonitrile as that of the active iodinating agent, and then the resultant solution was charged into the 10 ml syringe, which was connected to the feed tube of the high-speed mixer. Each syringe was set on a syringe pump, and flow rate from each syringe was adjusted to be 3.0 ml/min. The iodinating reaction was initiated by feeding each solution into the high-speed mixer. Sum of feed linear velocity for each solution was 50.9 cm/sec. The reaction solution obtained by the reaction displayed pale yellow color.

After completion of feeding solutions, the aqueous layer and the ether layer were separated. The ether layer was concentrated in vacuo, and the residue was loaded on a 10 cm silica gel column, followed by elution of reaction products from the column with 100 ml of ether. The solvent was concentrated in vacuo, and then 30 ml of a saturated sodium bicarbonate aqueous solution and 50 ml of hexane were added thereto, to carry out extraction. Two layers were separated, and the hexane layer was concentrated to dryness in vacuo, to yield 209.6 mg of a reaction product.

NMR analysis and GC analysis of the reaction product gave 72.5 mg of fluorene, 124.9 mg (0.428 mmol) of 2-iodo-9H-fluorene and 12.2 mg (0.029 mmol) of 2,7-diiodo-9H-fluorene. Namely, ratio of the production rates of mono-iodized product and di-iodized product was 93.6:6.4.

Example 1-9

Iodinating reaction was carried out using the similar apparatus to that in Example 1-8 by setting the reaction temperature at 25° C., to obtain 223.3 mg of a reaction product. The reaction solution obtained by the reaction displayed pale yellow color. NMR analysis and GC analysis of the reaction product gave 63.3 mg of fluorene, 148.1 mg (0.507 mmol) of 2-iodo-9H-fluorene and 11.8 mg (0.028 mmol) of 2,7-diiodo-9H-fluorene. Namely, ratio of the production rates of mono-iodized product and di-iodized product was 94.7:5.3.

Example 1-10

A flow reactor, in which a Teflon tube having an outer diameter of 1/16 inch, an inner diameter of 0.5 mm, and a length of 2 m, as a reaction section, was connected to an exit of a high-speed mixer (produced by IMM, Trade Name: SIMM-V2) having an equivalent diameter of 80 μm, was provided. To the feed inlet of the high-speed mixer, a syringe was connected via a Teflon tube having an outer diameter of 1/16 inch and an inner diameter of 0.5 mm.

Into a 100 ml Erlenmeyer flask, 30 ml of a saturated sodium bicarbonate aqueous solution, 1 ml of a saturated sodium thiosulfate aqueous solution, and 30 ml of diethyl ether were charged, and the solution was cooled to 0° C. on an ice-water bath while stirred with a magnetic stirrer. The high-speed mixer and the reaction section were also immersed into an ice-water bath to be cooled to 0° C. The exit of the reaction section was introduced into water layer in the Erlenmeyer flask.

Total amount of the active iodinating agent obtained in the above-described Reference Example was connected to the feed tube of the high-speed mixer. 154.2 mg (1.00 mmol) of biphenyl was dissolved in the same amount of acetonitrile as that of the active iodinating agent, and then the resultant solution was charged into the 10 ml syringe, which was connected to the feed tube of the high-speed mixer. Each syringe was set on a syringe pump, and flow rate from each syringe was adjusted to be 3.0 ml/min. The iodinating reaction was initiated by feeding each solution into the high-speed mixer. Sum of feed linear velocity for each solution was 50.9 cm/sec. The reaction solution obtained by the reaction displayed pale yellow color.

After completion of feeding solutions, the aqueous layer and the ether layer were separated. The ether layer was concentrated in vacuo, and the residue was loaded on a 10 cm silica gel column, followed by elution of reaction products from the column with 100 ml of ether. The solvent was concentrated in vacuo, and then 30 ml of a saturated sodium bicarbonate aqueous solution and 50 ml of hexane were added thereto, to carryout extraction. Two layers were separated, and the hexane layer was concentrated to dryness in vacuo, to yield 223.2 mg of a reaction product. NMR analysis and GC analysis of the reaction product gave 50.8 mg of biphenyl, 151.8 mg (0.542 mmol) of 4-iodobiphenyl and 20.6 mg (0.051 mmol) of 4,4'-diiodobiphenyl. Namely, ratio of the production rates of mono-iodized product and di-iodized product was 91.4:8.6.

Example 1-11

Reaction and post-treatment were carried out under the similar conditions to those in Example 1-1, except that an amount of 1,3-dimethoxybenzene was reduced to 112 mg (0.81 mmol), to obtain 204 mg of a reaction product. The reaction solution obtained by the reaction displayed pale yellow color.

NMR analysis and GC analysis of the reaction product gave 4.1 mg of 1,3-dimethoxybenzene, 184.3 mg (0.698 mmol) of 4-iodo-1,3-dimethoxybenzene and 15.5 mg (0.040 mmol) of 4,6-diiodo-1,3-dimethoxybenzene. Namely, ratio of the production rates of mono-iodized product and di-iodized product was 94.6:5.4.

Example 1-12

Reaction and post-treatment were carried out under the similar conditions to those in Example 1-6, except that an amount of 1,2-dimethoxybenzene was reduced to 110 mg (0.80 mmol), to obtain 204 mg of a reaction product. The reaction solution obtained by the reaction displayed pale yellow color.

NMR analysis and GC analysis of the reaction product gave 4.1 mg of 1,2-dimethoxybenzene, 184.3 mg (0.662 mmol) of 4-iodo-1,2-dimethoxybenzene and 7.7 mg (0.020 mmol) of 4,5-diiodo-1,2-dimethoxybenzene. Namely, ratio of the production rates of mono-iodized product and di-iodized product was 97.1:2.9.

Example 1-13

A flow reactor, in which a Teflon tube having an outer diameter of 1/16 inch, an inner diameter of 0.5 mm, and a length of 2 m, as a reaction section, was connected to an exit of a high-speed mixer (produced by IMM, Trade Name: SIMM-V2) having an equivalent diameter of 80 μm, was provided. To the feed inlet of the high-speed mixer, a syringe was connected via a Teflon tube having an outer diameter of 1/16 inch and an inner diameter of 0.5 mm.

Into a 100 ml Erlenmeyer flask, 30 ml of a saturated sodium bicarbonate aqueous solution, 1 ml of a saturated sodium thiosulfate aqueous solution, and 30 ml of diethyl ether were charged, and the solution was warmed to 40° C. on a hot-water bath while stirred with a magnetic stirrer. The high-speed mixer and the reaction section were also immersed into a hot-water bath to be warmed to 40° C. The exit of the reaction section was introduced into water layer in the Erlenmeyer flask.

Total amount of the active iodinating agent obtained in the above-described Reference Example was connected to the feed tube of the high-speed mixer. 62.8 mg (0.454 mmol) of 1,3-dimethoxybenzene was dissolved in the same amount of acetonitrile as that of the active iodinating agent, and then the resultant solution was charged into the 10 ml syringe, which was connected to the feed tube of the high-speed mixer. Each syringe was set on a syringe pump, and flow rate from each syringe was adjusted to be 3.0 ml/min. The iodinating reaction was initiated by feeding each solution into the high-speed mixer. Sum of feed linear velocity for each solution was 50.9 cm/sec. The reaction solution obtained by the reaction displayed pale yellow color.

After completion of feeding solutions, the aqueous layer and the ether layer were separated. The ether layer was concentrated in vacuo, and the residue was loaded on a 10 cm silica gel column, followed by elution of reaction products from the column with 100 ml of ether. The solvent was concentrated in vacuo, and then 30 ml of a saturated sodium bicarbonate aqueous solution and 50 ml of hexane were added thereto, to carry out extraction. Two layers were separated, and the hexane layer was concentrated to dryness in vacuo, to yield 148.2 mg of a reaction product.

NMR analysis and GC analysis of the reaction product gave 9.1 mg of 1,3-dimethoxybenzene, 134.8 mg (0.346 mmol) of 4,6-diiodo-1,3-dimethoxybenzene and 4.3 mg (0.016 mmol) of 4-iodo-1,3-dimethoxybenzene. Namely, ratio of the production rates of di-iodized product and mono-iodized product was 95.6:4.4.

Example 1-14

Into a 100 ml Erlenmeyer flask, 1,431.0 mg (8.81 mmol) of iodine monochloride and 70.47 ml (55.11 g) of acetonitrile were charged, to be used as an active iodinating agent [the solution was prepared so as to contain 162.4 mg (1.00 mmol) of iodine monochloride in 8 ml]. Similarly, into a 100 ml Erlenmeyer flask, 1,246.0 mg (9.02 mmol) of 1,3-dimethoxybenzene and 71.46 ml (55.88 g) of acetonitrile were charged, to be used as a substrate [the solution was prepared so as to contain 139.5 mg (1.01 mmol) of 1,3-dimethoxybenzene in 8 ml].

A flow reactor, in which a Teflon tube having an outer diameter of 1/16 inch, an inner diameter of 0.5 mm, and a length of 2 m, as a reaction section, was connected to an exit of a high-speed mixer (produced by IMM, Trade Name: SIMM-V2) having an equivalent diameter of 80 μm, was provided. To the feed inlet of the high-speed mixer, a syringe was connected via a Teflon tube having an outer diameter of 1/16 inch and an inner diameter of 0.5 mm.

Into a 100 ml Erlenmeyer flask, 30 ml of a saturated sodium bicarbonate aqueous solution, 1 ml of a saturated sodium thiosulfate aqueous solution, and 30 ml of diethyl ether were charged, and the solution was stirred with a magnetic stirrer.

The reaction section were immersed into a hot-water bath at 50° C. The exit of the reaction section was introduced into water layer in the Erlenmeyer flask.

The iodine monochloride/acetonitrile solution (8 ml) prepared as described above was charged into the 10 ml syringe, which was connected to the feed tube of the high-speed mixer. Another 1,3-dimethoxybenzene/acetonitrile solution (8 ml) was charged into the 10 ml syringe, which was connected to the feed tube of the high-speed mixer. Each syringe was set on a syringe pump, and flow rate from each syringe was adjusted to be 3.0 ml/min. The iodinating reaction was initiated by feeding each solution into the high-speed mixer. The sum of feed linear velocity for each solution was 50.9 cm/sec. The reaction solution obtained by the reaction displayed pale yellow color.

After completion of feeding solutions, the aqueous layer and the ether layer were separated. The ether layer was concentrated in vacuo, and then 30 ml of a saturated sodium bicarbonate aqueous solution and 50 ml of hexane were added thereto, to carry out extraction. Two layers were separated, and the hexane layer was concentrated to dryness in vacuo, to yield 211.6 mg of a reaction product.

NMR analysis and GC analysis of the reaction product gave 45.5 mg of 1,3-dimethoxybenzene, 164.2 mg (0.622 mmol) of 4-iodo-1,3-dimethoxybenzene and 1.9 mg (0.005 mmol) of 4,6-diiodo-1,3-dimethoxybenzene. Namely, ratio of the production rates of di-iodized product and mono-iodized product was 99.2:0.8.

Comparative Example 1-1

Into a 50 ml round-bottom flask, 138 mg (1.0 mmol) of 1,3-dimethoxybenzene, 8 ml of acetonitrile were charged together with a stirring bar. The solution was cooled to 0° C. on an ice-water bath while stirred with a magnetic stirrer. Total amount of the active iodinating agent prepared in the above-described Reference Example was added thereto, and the iodinating reaction was carried out at 0° C. for 1 hour.

The reaction solution was concentrated in vacuo, and the residue was loaded on a 10 cm silica gel column, followed by elution of reaction products from the column with 100 ml of ether. The solvent was concentrated in vacuo, and then 30 ml of a saturated sodium bicarbonate aqueous solution and 50 ml of hexane were added thereto, to carry out extraction. In this case, the reaction solution displayed brownish color due to the presence of free iodine. Two layers were separated, and the hexane layer was concentrated to dryness in vacuo, to yield 255.5 mg of a reaction product.

NMR analysis and GC analysis of the reaction product gave 31.8 mg of 1,3-dimethoxybenzene, 165.8 mg (0.628 mmol) of 4-iodo-1,3-dimethoxybenzene and 38.0 mg (0.097 mmol) of 4,6-diiodo-1,3-dimethoxybenzene. Namely, ratio of the production rates of mono-iodized product and di-iodized product was 86.6:13.4.

Comparative Example 1-2

Into a 50 ml round-bottom flask, 138 mg (1.0 mmol) of 1,2-dimethoxybenzene, 8 ml of acetonitrile were charged together with a stirring bar. The solution was cooled to 0° C. on an ice-water bath while stirred with a magnetic stirrer. Total amount of the active iodinating agent prepared in the above-described Reference Example was added thereto, and the iodinating reaction was carried out at 0° C. for 1 hour.

The reaction solution was concentrated in vacuo, and the residue was loaded on a 10 cm silica gel column, followed by elution of reaction products from the column with 100 ml of ether. The solvent was concentrated in vacuo, and then 30 ml of a saturated sodium bicarbonate aqueous solution and 50 ml of hexane were added thereto, to carry out extraction. In this case, the reaction solution displayed brownish color due to the presence of free iodine. Two layers were separated, and the hexane layer was concentrated to dryness in vacuo, to yield 205.6 mg of a reaction product.

NMR analysis and GC analysis of the reaction product gave 29.3 mg of 1,2-dimethoxybenzene, 168.6 mg (0.638 mmol) of 4-iodo-1,2-dimethoxybenzene and 12.2 mg (0.031 mmol) of 4,6-diiodo-1,3-dimethoxybenzene. Namely, ratio of the production rates of mono-iodized product and di-iodized product was 95.4:4.6.

Comparative Example 1-3

Into a 50 ml round-bottom flask, 138 mg (1.0 mmol) of 1,4-dimethoxybenzene, 8 ml of acetonitrile were charged together with a stirring bar. The solution was cooled to 0° C. on an ice-water bath while stirred with a magnetic stirrer. Total amount of the active iodinating agent prepared in the above-described Reference Example was added thereto, and the iodinating reaction was carried out at 0° C. for 1 hour. The reaction solution was concentrated in vacuo, and the residue was loaded on a 10 cm silica gel column, followed by elution of reaction products from the column with 100 ml of ether. The solvent was concentrated in vacuo, and then 30 ml of a saturated sodium bicarbonate aqueous solution and 50 ml of hexane were added thereto, to carryout extraction. Two layers were separated, and the hexane layer was concentrated to dryness in vacuo, to yield 223.2 mg of a reaction product.

NMR analysis and GC analysis of the reaction product gave 15.9 mg of 1,4-dimethoxybenzene, 168.6 mg (0.646 mmol) of 3-iodo-1,4-dimethoxybenzene and 36.8 mg (0.094 mmol) of 4,6-diiodo-1,3-dimethoxybenzene. Namely, ratio of the production rates of mono-iodized product and di-iodized product was 87.3:12.7.

Comparative Example 1-4

Into a 50 ml round-bottom flask, 166.2 mg (1.00 mmol) of fluorene, 8 ml of acetonitrile were charged together with a stirring bar. The solution was cooled to 0° C. on an ice-water bath while stirred with a magnetic stirrer. Total amount of the active iodinating agent prepared in the above-described Reference Example was added thereto, and the iodinating reaction was carried out at 0° C. for 1 hour. The reaction solution was concentrated in vacuo, and the residue was loaded on a 10 cm silica gel column, followed by elution of reaction products from the column with 100 ml of ether. The solvent was concentrated in vacuo, and then 30 ml of a saturated sodium bicarbonate aqueous solution and 50 ml of hexane were added thereto, to carry out extraction. Two layers were separated, and the hexane layer was concentrated to dryness in vacuo, to yield 280.8 mg of a reaction product.

NMR analysis and GC analysis of the reaction product gave 62.3 mg of fluorene, 178.3 mg (0.610 mmol) of 2-iodo-9H-fluorene and 40.2 mg (0.096 mmol) of 2,7-diiodo-9H-fluorene. Namely, ratio of the production rates of mono-iodized product and di-iodized product was 86.4:13.6.

Comparative Example 1-5

Into a 50 ml round-bottom flask, 154.2 mg (1.00 mmol) of biphenyl, 8 ml of acetonitrile were charged together with a stirring bar. The solution was cooled to 0° C. on an ice-water bath while stirred with a magnetic stirrer. Total amount of the active iodinating agent prepared in the above-described Reference Example was added thereto, and the iodinating reaction was carried out at 0° C. for 1 hour. The reaction solution was concentrated in vacuo, and the residue was loaded on a 10 cm silica gel column, followed by elution of reaction products from the column with 100 ml of ether. The solvent was concentrated in vacuo, and then 30 ml of a saturated sodium bicarbonate aqueous solution and 50 ml of hexane were added thereto, to carry out extraction. Two layers were separated, and the hexane layer was concentrated to dryness in vacuo, to yield 172.2 mg of a reaction product.

NMR analysis and GC analysis of the reaction product gave 18.9 mg of biphenyl, 123.1 mg (0.440 mmol) of 4-iodobiphenyl and 30.2 mg (0.074 mmol) of 4,4'-diiodobiphenyl. Namely, ratio of the production rates of mono-iodized product and di-iodized product was 85.5:14.5.

Comparative Example 1-6

Into a 50 ml round-bottom flask, 61.6 mg (0.446 mmol) of 1,3-dimethoxybenzene, 8 ml of acetonitrile were charged together with a stirring bar. The solution was cooled to 0° C. on an ice-water bath while stirred with a magnetic stirrer. Total amount of the active iodinating agent prepared in the above-described Reference Example was added thereto, and the reaction was carried out at 40° C. for 1 hour.

The reaction solution was concentrated in vacuo, and the residue was loaded on a 10 cm silica gel column, followed by elution of reaction products from the column with 100 ml of ether. The solvent was concentrated in vacuo, and then 30 ml of a saturated sodium bicarbonate aqueous solution and 50 ml of hexane were added thereto, to carry out extraction. In this case, the reaction solution displayed brownish color due to the presence of free iodine. Two layers were separated, and the hexane layer was concentrated to dryness in vacuo, to yield 107.3 mg of a reaction product.

NMR analysis and GC analysis of the reaction product gave 6.3 mg of 1,3-dimethoxybenzene, 83.5 mg (0.214 mmol) of 4,6-diiodo-1,3-dimethoxybenzene and 17.5 mg (0.066 mmol) of 4-iodo-1,3-dimethoxybenzene. Namely, ratio of the production rates of di-iodized product and mono-iodized product was 76.4:23.6.

Comparative Example 1-7

Into a 30 ml Erlenmeyer flask, 162.4 mg (1.00 mmol) of iodine monochloride and 8 ml of acetonitrile were charged, to be used as an active iodinating agent. Similarly, into a 30 ml Erlenmeyer flask, 138.0 mg (1.00 mmol) of 1,3-dimethoxybenzene and 8 ml of acetonitrile were charged, to be used as a substrate.

Each solution thus prepared was charged into a 100 ml round-bottom flask immersed into a hot-water bath at 50° C. Then, the solution was stirred for one hour under nitrogen gas stream. 30 ml of a saturated sodium bicarbonate aqueous solution, 2 ml of a saturated sodium thiosulfate aqueous solution and 30 ml of diethyl ether were added thereto, to complete the reaction.

After the reaction was completed, the aqueous layer and the ether layer were separated. The ether layer was concentrated in vacuo, and then 30 ml of a saturated sodium bicarbonate aqueous solution and 50 ml of hexane were added thereto, to carry out extraction. In this case, the reaction solution displayed brownish color due to the presence of free iodine. Two layers were separated, and the hexane layer was concentrated to dryness in vacuo, to yield 243.4 mg of a reaction product.

NMR analysis and GC analysis of the reaction product gave 17.0 mg of 1,3-dimethoxybenzene, 209.4 mg (0.793 mmol) of 4-iodo-1,3-dimethoxybenzene and 17.0 mg (0.044 mmol) of 4,6-diiodo-1,3-dimethoxybenzene. Namely, ratio of the production rates of mono-iodized product and di-iodized product was 94.7:5.3.

TABLE 2

| | Substrate | n | m | Feed linear velocity (cm/sec) | Reaction time(sec) | Yield of m-molar product (%) | Selectivity for m-molar product (%) | Amount of active iodinating agent per mole of substrate (based on I, mole) |
|---|---|---|---|---|---|---|---|---|
| Example 1-1 | 1,3-Dimethoxybenzene | 4 | 1 | 50.9 | 3.9 | 75.6 | 98.4 | 1.0 |
| Example 1-2 | 1,3-Dimethoxybenzene | 4 | 1 | 3.4 | 58.5 | 77.7 | 91.8 | 1.0 |
| Example 1-3 | 1,3-Dimethoxybenzene | 4 | 1 | 17.0 | 11.7 | 73.1 | 96.6 | 1.0 |
| Example 1-4 | 1,3-Dimethoxybenzene | 4 | 1 | 34.0 | 10.4 | 70.2 | 98.0 | 1.0 |
| Example 1-5 | 1,3-Dimethoxybenzene | 4 | 1 | 84.9 | 2.34 | 73.2 | 98.8 | 1.0 |
| Example 1-6 | 1,2-Dimethoxybenzene | 4 | 1 | 50.9 | 3.9 | 61.3 | 98.9 | 1.0 |
| Example 1-7 | 1,4-Dimethoxybenzene | 4 | 1 | 50.9 | 3.9 | 70.1 | 94.1 | 1.0 |
| Example 1-8 | Fluorene | 8 | 1 | 50.9 | 3.9 | 42.8 | 93.6 | 1.0 |
| Example 1-9 | Fluorene | 8 | 1 | 50.9 | 3.9 | 50.7 | 94.7 | 1.0 |
| Example 1-10 | Biphenyl | 10 | 1 | 50.9 | 3.9 | 54.2 | 91.4 | 1.0 |
| Example 1-11 | 1,3-Dimethoxybenzene | 4 | 1 | 50.9 | 3.9 | 86.2 | 94.6 | 1.2 |
| Example 1-12 | 1,2-Dimethoxybenzene | 4 | 1 | 50.9 | 3.9 | 82.8 | 97.1 | 1.2 |
| Example 1-13 | 1,3-Dimethoxybenzene | 4 | 2 | 50.9 | 3.9 | 76.2 | 95.6 | 2.2 |
| Example 1-14 | 1,3-Dimethoxybenzene | 4 | 1 | 50.9 | 3.9 | 61.6 | 99.2 | 1.0 |
| Com. Ex. 1-1 | 1,3-Dimethoxybenzene | 4 | 1 | — | 3,600 | 62.8 | 86.6 | 1.0 |
| Com. Ex. 1-2 | 1,2-Dimethoxybenzene | 4 | 1 | — | 3,600 | 63.8 | 95.4 | 1.0 |
| Com. Ex. 1-3 | 1,4-Dimethoxybenzene | 4 | 1 | — | 3,600 | 64.6 | 87.3 | 1.0 |
| Com. Ex. 1-4 | Fluorene | 8 | 1 | — | 3,600 | 61.0 | 86.4 | 1.0 |
| Com. Ex. 1-5 | Biphenyl | 10 | 1 | — | 3,600 | 44.0 | 85.5 | 1.0 |
| Com. Ex. 1-6 | 1,3-Dimethoxybenzene | 4 | 2 | — | 3,600 | 48.0 | 76.4 | 2.2 |
| Com. Ex. 1-7 | 1,3-Dimethoxybenzene | 4 | 1 | — | 3,600 | 79.3 | 94.7 | 1.0 |

Com. Ex.: Comparative Example (Results)

(1) Based on the experimental results of Examples 1-1 to 1-5, relationship between feed linear velocity and selectivity for mono-iodized product is shown in FIG. 1. It is noted from FIG. 1 that in the case when 1,3-dimethoxybenzene is used as a substrate, the selectivity for mono-iodized product is the highest at total feed linear velocity of an aromatic compound solution and an active iodinating agent solution of 50.9 cm/sec, and that when the total feed linear velocity is below 17 cm/sec, the selectivity for mono-iodized product sharply decreases.

(2) Comparison results of Example 1-1 and Comparative Example 1-1 in the case when 1,3-dimethoxybenzene as an aromatic compound was iodized are shown in Table 3. It is apparently noted from Table 3 that the reaction in Comparative Example 1-1 (batch system) shows the selectivity for mono-iodized product of 80 s %, whereas use of the micro-reactor can improve the selectivity up to 98% or more within an extremely short time. In addition, it is also found that yield can be similarly improved.

The reaction time in Example 1-1 was only 3.9 sec, whereas Comparative Example 1-1 required 3,600 sec. From this fact, the present invention using a micro-reactor is found to be a method which is exactly excellent in production efficiency.

TABLE 3

|  | Reaction temperature | Reaction time (sec) | Yield | Selectivity for mono-iodized product |
| --- | --- | --- | --- | --- |
| Example 1-1 | 0° C. | 3.9 | 75.6% | 98.4% |
| Comparative Example 1-1 | 0° C. | 3,600 | 62.8% | 86.6% |

(3) It is noted from the comparison between Example 1-13 and Comparative Example 1-6 that when di-iodized product of an aromatic compound is synthesized by using a micro-reactor according to the present invention, di-iodized product can be synthesized at high selectivity, and yield of di-iodized product can be also improved.

(4) It is noted from the comparisons of each Example with each Comparative Example that when an aromatic compound is iodized using a micro-reactor, coloring to iodine color of the reaction solution obtained by the reaction can be suppressed. Accordingly, simplification of additional purification step can be attained, which lead to reduce a cost for synthesis.

<Effect of Molar Ratio of Substrate on Selectivity for Mono-iodized Product>

By the following experiments, an effect of molar ratio of substrate on selectivity for mono-iodized product was examined.

Example 2-1

A flow reactor, in which a Teflon tube having an outer diameter of 1/16 inch, an inner diameter of 0.5 mm, and a length of 2 m, as a reaction section, was connected to an exit of a high-speed mixer (produced by IMM, Trade Name: SIMM-V2) having an equivalent diameter of 80 µm, was provided. To the feed inlet of the high-speed mixer, a syringe was connected via a Teflon tube having an outer diameter of 1/16 inch and an inner diameter of 0.5 mm.

Into a 100 ml Erlenmeyer flask, 30 ml of a saturated sodium bicarbonate aqueous solution, 1 ml of a saturated sodium thiosulfate aqueous solution, and 30 ml of diethyl ether were charged, and the solution was cooled to 0° C. on an ice-water bath while stirred with a magnetic stirrer. The high-speed mixer and the reaction section were also immersed into an ice-water bath to be cooled to 0° C. The exit of the reaction section was introduced into water layer in the Erlenmeyer flask.

Total amount of the active iodinating agent obtained in the above-described Reference Example was connected to the feed tube of the high-speed mixer. At the same time, was dissolved in the same amount of acetonitrile to the active iodinating agent, then charged into the 10 ml syringe, which was connected to the feed tube of the high-speed mixer. Each syringe was set on a syringe pump, and flow rate from each syringe was adjusted to be 3.0 ml/min. The iodinating reaction was initiated by feeding each solution into the high-speed mixer. The sum of feed linear velocity for each solution was 50.9 cm/sec. The reaction liquid obtained by the reaction took on pale yellow color.

Total amount of the active iodinating agent obtained in the above-described Reference Example was connected to the feed tube of the high-speed mixer. 136.8 mg (0.99 mmol, molar ratio of iodine (based on atom)/substrate=1.01) of 1,3-dimethoxybenzene was dissolved in the same amount of acetonitrile as that of the active iodinating agent, and then the resultant solution was charged into the 10 ml syringe, which was connected to the feed tube of the high-speed mixer. Each syringe was set on a syringe pump, and flow rate from each syringe was adjusted to be 3.0 ml/min. The iodinating reaction was initiated by feeding each solution into the high-speed mixer. Sum of feed linear velocity for each solution was 50.9 cm/sec. The reaction solution obtained by the reaction displayed pale yellow color.

After completion of feeding solutions, the aqueous layer and the ether layer were separated. The ether layer was concentrated in vacuo, and the residue was loaded on a 10 cm silica gel column, followed by elution of reaction products from the column with 100 ml of ether. The solvent was concentrated in vacuo, and then 30 ml of a saturated sodium bicarbonate aqueous solution and 50 ml of hexane were added thereto, to carry out extraction. Two layers were separated, and the hexane layer was concentrated to dryness in vacuo, to yield a reaction product.

NMR analysis and GC analysis of the reaction product gave 180.4 mg (0.683 mmol=yield of 69.0%) of 4-iodo-1,3-dimethoxybenzene and 6.7 mg (0.017 mmol=yield of 1.7%) of 4,6-diiodo-1,3-dimethoxybenzene. Namely, ratio of the production rates of mono-iodized product and di-iodized product was 97.6:2.4.

Example 2-2

Iodinating reaction was carried out using similar apparatus and procedure to those in the above-described Example 2-1, except that an amount of 1,3-dimethoxybenzene as a raw material was changed to 131.6 mg (0.95 mmol; molar ratio of iodine/substrate=1.05).

NMR analysis and GC analysis of the reaction product gave 171.9 mg (0.651 mmol=yield of 68.5%) of 4-iodo-1,3-dimethoxybenzene and 4.8 mg (0.012 mmol=yield of 1.3%) of 4,6-diiodo-1,3-dimethoxybenzene. Namely, ratio of the production rates of mono-iodized product and di-iodized product was 98.2:1.8.

Example 2-3

Iodinating reaction was carried out using similar apparatus and procedure to those in the above-described Example 2-1, except that an amount of 1,3-dimethoxybenzene as a raw material was changed to 124.5 mg (0.90 mmol; molar ratio of iodine/substrate=1.11).

NMR analysis and GC analysis of the reaction product gave 177.9 mg (0.674 mmol=yield of 74.8%) of 4-iodo-1,3-dimethoxybenzene and 8.0 mg (0.020 mmol=yield of 2.3%) of 4,6-diiodo-1,3-dimethoxybenzene. Namely, ratio of the production rates of mono-iodized product and di-iodized product was 97.1:2.9.

Example 2-4

Iodinating reaction was carried out using similar apparatus and procedure to those in the above-described Example 2-1, except that an amount of 1,3-dimethoxybenzene as a raw material was changed to 112.3 mg (0.81 mmol; molar ratio of iodine/substrate=1.23).

NMR analysis and GC analysis of the reaction product gave 166.8 mg (0.632 mmol=yield of 77.7%) of 4-iodo-1,3-dimethoxybenzene and 13.0 mg (0.033 mmol=yield of 4.1%) of 4,6-diiodo-1,3-dimethoxybenzene. Namely, ratio of the production rates of mono-iodized product and di-iodized product was 95.0:5.0.

Comparative Example 2-1

Into a 50 ml round-bottom flask, 138.2 mg (1.00 mmol; molar ratio of iodine/substrate=1.00) of 1,3-dimethoxybenzene, 8 ml of acetonitrile were charged together with a stirring bar. The solution was cooled to 0° C. on an ice-water bath while stirred with a magnetic stirrer. Total amount of the active iodinating agent prepared in the above-described Reference Example was added thereto, and the iodinating reaction was carried out at 0° C. for 1 hour.

The reaction solution was concentrated in vacuo, and the residue was loaded on a 10 cm silica gel column, followed by elution of reaction products from the column with 100 ml of ether. The solvent was concentrated in vacuo, and then 30 ml of a saturated sodium bicarbonate aqueous solution and 50 ml of hexane were added thereto, to carry out extraction. In this case, the reaction solution displayed brownish color due to the presence of free iodine. Two layers were separated, and the hexane layer was concentrated to dryness in vacuo, to yield a reaction product.

NMR analysis and GC analysis of the reaction product gave 163.1 mg (0.618 mmol=yield of 61.8%) of 4-iodo-1,3-dimethoxybenzene and 28.5 mg (0.073 mmol=yield of 7.3%) of 4,6-diiodo-1,3-dimethoxybenzene. Namely, ratio of the production rates of mono-iodized product and di-iodized product was 89.4:10.6.

Comparative Example 2-2

Iodinating reaction was carried out using similar apparatus and procedure to those in the above-described Example 2-1, except that an amount of 1,3-dimethoxybenzene as a raw material was changed to 132.8 mg (0.96 mmol; molar ratio of iodine/substrate=1.04).

NMR analysis and GC analysis of the reaction product gave 156.9 mg (0.594 mmol=yield of 62.0%) of 4-iodo-1,3-dimethoxybenzene and 29.9 mg (0.113 mmol=yield of 11.8%) of 4,6-diiodo-1,3-dimethoxybenzene. Namely, ratio of the production rates of mono-iodized product and di-iodized product was 84.0:16.0.

Comparative Example 2-3

Iodinating reaction was carried out using similar apparatus and procedure to those in the above-described Example 2-1, except that an amount of 1,3-dimethoxybenzene as a raw material was changed to 125.6 mg (0.91 mmol; molar ratio of iodine/substrate=1.10).

NMR analysis and GC analysis of the reaction product gave 150.9 mg (0.572 mmol=yield of 62.9%) of 4-iodo-1,3-dimethoxybenzene and 59.3 mg (0.152 mmol=yield of 16.7%) of 4,6-diiodo-1,3-dimethoxybenzene. Namely, ratio of the production rates of mono-iodized product and di-iodized product was 79.0:21.0.

Comparative Example 2-4

Iodinating reaction was carried out using similar apparatus and procedure to those in the above-described Example 2-1, except that an amount of 1,3-dimethoxybenzene as a raw material was changed to 111.4 mg (0.81 mmol; molar ratio of iodine/substrate=1.24).

NMR analysis and GC analysis of the reaction product gave 95.5 mg (0.362 mmol=yield of 44.9%) of 4-iodo-1,3-dimethoxybenzene and 57.3 mg (0.147 mmol=yield of 18.2%) of 4,6-diiodo-1,3-dimethoxybenzene. Namely, ratio of the production rates of mono-iodized product and di-iodized product was 71.1:28.9.

Figure 2:
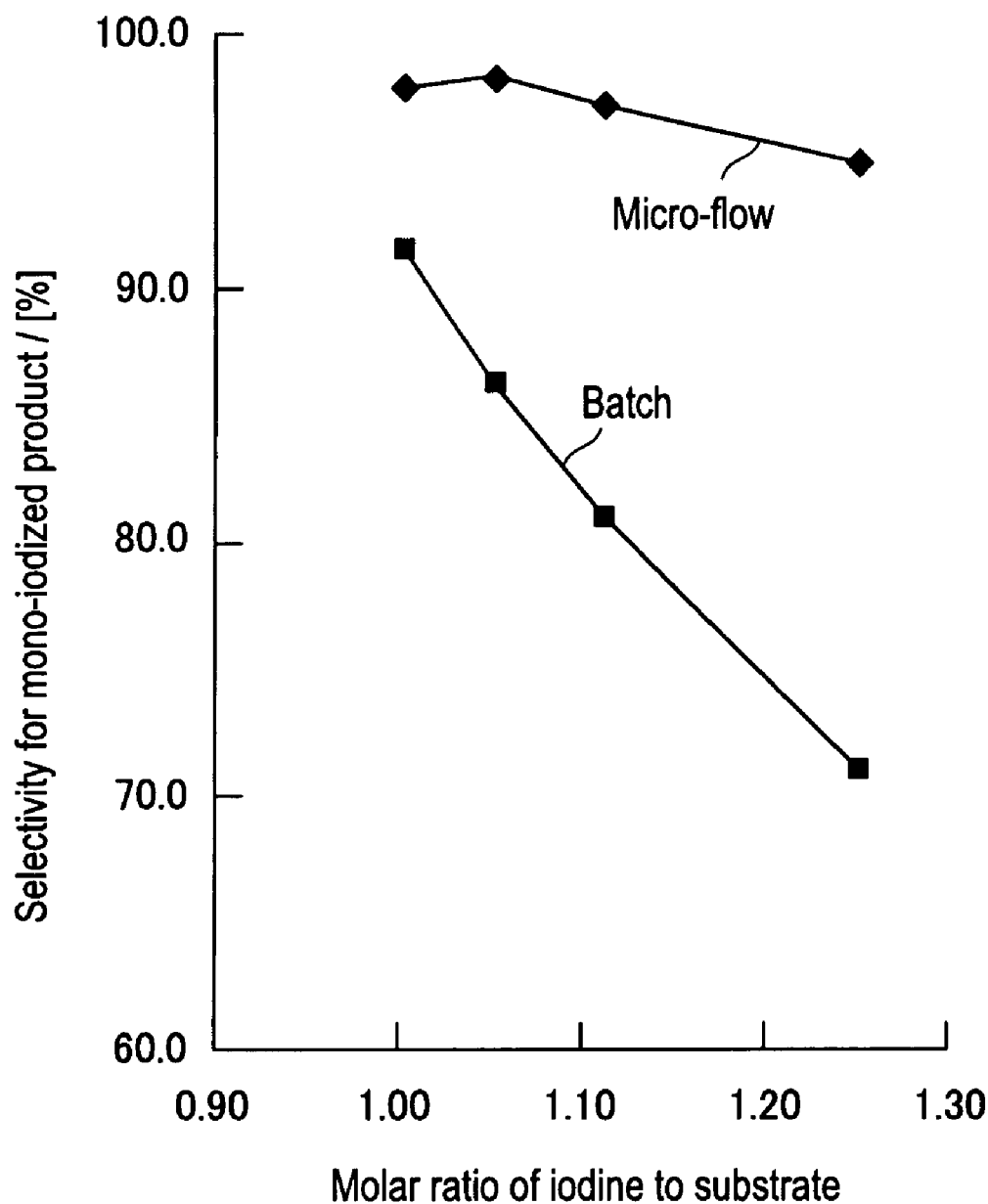
FIG. 2 is a graph showing an effect of molar ratio of substrate on selectivity for mono-iodized product in Examples 2-1 to 2-4 and Comparative Examples 2-1 to 2-4.

The results described above are summarized in Table 4. Effects of the molar ratio of substrate (1,3-dimethoxybenzene) on the selectivity for mono-iodized product in each Example and each Comparative Example are shown in FIG. 2 as a graph.

TABLE 4

|  | I/substrate (molar ratio) | Reaction system | Yield of mono-iodized product | Yield of di-iodized product | Selectivity for mono-iodized product |
|---|---|---|---|---|---|
| Example 2-1 | 1.01 | Micro-flow | 69.0% | 1.7% | 97.6% |
| Example 2-2 | 1.05 | Micro-flow | 68.5% | 1.3% | 98.2% |
| Example 2-3 | 1.11 | Micro-flow | 74.8% | 2.3% | 97.1% |
| Example 2-4 | 1.23 | Micro-flow | 77.7% | 4.1% | 95.0% |
| Comparative Example 2-1 | 1.00 | Batch | 61.8% | 7.3% | 89.4% |
| Comparative Example 2-2 | 1.04 | Batch | 62.0% | 11.8% | 84.0% |
| Comparative Example 2-3 | 1.10 | Batch | 62.9% | 16.7% | 79.0% |
| Comparative Example 2-4 | 1.24 | Batch | 44.9% | 18.2% | 71.1% |

Heretofore, when a mono-iodized product is to be prepared, for example, from the viewpoint of suppressing formation of by-products such as di-iodized product and tri-iodized product, amount of iodine added to the reaction product had been set generally at a slightly lower level (namely, molar ratio of iodine/substrate had been set at a level lower than 1.0), which has caused a problem that sufficient yield is difficult to be attained. On the contrary, according to the present invention, by carrying out the reaction using a micro-reactor, mono-iodized product as a desired product has been found to be able to be prepared in high selectivity and in high yield, as shown in Table 4 and FIG. 2, even when molar ratio of iodine to substrate is set at a level higher than 1.0.

The entire disclosure of Japanese Patent Application No. 2005-001693 filed on Jan. 6, 2005 including specification, claims, drawings and summary are incorporated herein by reference in its entirety.

The invention claimed is:

1. A method for producing an aromatic iodide, wherein an aromatic compound and an active iodinating agent are fed into a flow reactor equipped with a high-speed mixer and hydrogen atom on the aromatic ring of said aromatic compound is continuously substituted by iodine atom.

2. The method for producing an aromatic iodide according to claim 1, wherein said active iodinating agent is fed into said flow reactor in a ratio of (m−0.4) moles to (m+0.4) moles (based on iodine atom) (wherein m is an integer satisfying: $1 \leq m \leq n-1$) to 1 mole of said aromatic compound having not less than n (wherein n is an integer of 2 or more) hydrogen atoms bonding to the aromatic ring to substitute said hydrogen atom by m moles of iodine.

3. The method for producing an aromatic iodide according to claim 1, wherein in said high-speed mixer, a mixing time of said aromatic compound and said active iodinating agent is shorter than the reaction time of said aromatic compound and said active iodinating agent.

4. The method for producing an aromatic iodide according to claim 1, wherein said active iodinating agent is fed into said flow reactor in a ratio of 0.9 moles to 1.3 moles (based on iodine atom) to 1 mole of said aromatic compound to obtain a mono-iodized product.

5. The method for producing an aromatic iodide according to claim 1, wherein said active iodinating agent is fed into said flow reactor in a ratio of 1.8 moles to 2.3 moles (based on iodine atom) to 1 mole of said aromatic compound to obtain a di-iodized product.

6. The method for producing an aromatic iodide according to claim 1, wherein said active iodinating agent is fed into said flow reactor in a ratio of 2.8 moles to 3.3 moles (based on iodine atom) to 1 mole of said aromatic compound to obtain a tri-iodized product.

7. The method for producing an aromatic iodide according to claim 1, wherein said active iodinating agent is a compound that comprises an iodonium cation as a reaction activator to be generated by electrolytic oxidation of iodine or electrolytic oxidation of iodine compound.

8. The method for producing an aromatic iodide according to claim 1, wherein said active iodinating agent is a compound that comprises an iodonium cation as a reaction activator to be generated by oxidation of iodine or iodine compound with an oxidizing agent.

9. The method for producing an aromatic iodide according to claim 1, wherein said high-speed mixer is a micro-mixer.

10. The method for producing an aromatic iodide according to claim 2, wherein in said high-speed mixer, a mixing time of said aromatic compound and said active iodinating agent is shorter than the reaction time of said aromatic compound and said active iodinating agent.

11. The method for producing an aromatic iodide according to claim 2, wherein said active iodinating agent is fed into said flow reactor in a ratio of 0.9 moles to 1.3 moles (based on iodine atom) to 1 mole of said aromatic compound to obtain a mono-iodized product.

12. The method for producing an aromatic iodide according to claim 3, wherein said active iodinating agent is fed into said flow reactor in a ratio of 0.9 moles to 1.3 moles (based on iodine atom) to 1 mole of said aromatic compound to obtain a mono-iodized product.

13. The method for producing an aromatic iodide according to claim 2, wherein said active iodinating agent is fed into said flow reactor in a ratio of 1.8 moles to 2.3 moles (based on iodine atom) to 1 mole of said aromatic compound to obtain a di-iodized product.

14. The method for producing an aromatic iodide according to claim 3, wherein said active iodinating agent is fed into said flow reactor in a ratio of 1.8 moles to 2.3 moles (based on iodine atom) to 1 mole of said aromatic compound to obtain a di-iodized product.

15. The method for producing an aromatic iodide according to claim 2, wherein said active iodinating agent is fed into said flow reactor in a ratio of 2.8 moles to 3.3 moles (based on iodine atom) to 1 mole of said aromatic compound to obtain a tri-iodized product.

16. The method for producing an aromatic iodide according to claim 3, wherein said active iodinating agent is fed into said flow reactor in a ratio of 2.8 moles to 3.3 moles (based on iodine atom) to 1 mole of said aromatic compound to obtain a tri-iodized product.

17. The method for producing an aromatic iodide according to claim 2, wherein said active iodinating agent is a compound that comprises an iodonium cation as a reaction activator to be generated by electrolytic oxidation of iodine or electrolytic oxidation of iodine compound.

18. The method for producing an aromatic iodide according to claim 3, wherein said active iodinating agent is a compound that comprises an iodonium cation as a reaction activator to be generated by electrolytic oxidation of iodine or electrolytic oxidation of iodine compound.

19. The method for producing an aromatic iodide according to claim 4, wherein said active iodinating agent is a compound that comprises an iodonium cation as a reaction activator to be generated by electrolytic oxidation of iodine or electrolytic oxidation of iodine compound.

20. The method for producing an aromatic iodide according to claim 5, wherein said active iodinating agent is a compound that comprises an iodonium cation as a reaction activator to be generated by electrolytic oxidation of iodine or electrolytic oxidation of iodine compound.

* * * * *